United States Patent [19]
Leverett

[11] Patent Number: 6,132,739
[45] Date of Patent: Oct. 17, 2000

[54] MAKEUP COMPOSITIONS AND METHODS OF MAKING SAME

[75] Inventor: Jesse C. Leverett, Rockford, Mich.

[73] Assignee: Amway Corporation, Ada, Mich.

[21] Appl. No.: 09/144,935

[22] Filed: Sep. 1, 1998

[51] Int. Cl.$^7$ .............................. A61K 6/00; A61K 7/00; A61K 7/42; A61K 7/021

[52] U.S. Cl. .................. 424/401; 424/59; 424/63

[58] Field of Search .................. 424/63, 401, 78.03, 424/59; 514/937, 844, 845

[56] References Cited

U.S. PATENT DOCUMENTS

| | | |
|---|---|---|
| 4,578,266 | 3/1986 | Tietjen et al. . |
| 4,665,107 | 5/1987 | Micale . |
| 4,707,293 | 11/1987 | Ferro . |
| 4,777,041 | 10/1988 | Mercado . |
| 4,778,836 | 10/1988 | Farrar et al. ............... 524/35 |
| 4,839,163 | 6/1989 | Busch, Jr. . |
| 5,028,417 | 7/1991 | Bhat et al. . |
| 5,032,390 | 7/1991 | Iwaya et al. . |
| 5,066,485 | 11/1991 | Brieva et al. ............... 424/63 |
| 5,093,099 | 3/1992 | Haishi et al. . |
| 5,143,722 | 9/1992 | Hollenberg et al. . |
| 5,188,831 | 2/1993 | Nicoll et al. . |
| 5,216,033 | 6/1993 | Pereira et al. . |
| 5,250,289 | 10/1993 | Boothroyd et al. . |
| 5,306,486 | 4/1994 | McCook et al. . |
| 5,340,567 | 8/1994 | Cole et al. . |
| 5,447,723 | 9/1995 | Sköld . |
| 5,476,660 | 12/1995 | Somasundaran . |
| 5,478,562 | 12/1995 | Cauwet et al. . |
| 5,486,354 | 1/1996 | Defossez et al. . |
| 5,501,850 | 3/1996 | Stein et al. . |
| 5,518,733 | 5/1996 | Lamothe et al. . |
| 5,543,135 | 8/1996 | Dahms . |
| 5,573,753 | 11/1996 | Tapley . |
| 5,599,529 | 2/1997 | Cowie . |
| 5,599,533 | 2/1997 | Stepniewski et al. . |
| 5,616,331 | 4/1997 | Allard et al. . |
| 5,670,139 | 9/1997 | Allard et al. . |
| 5,670,154 | 9/1997 | Hara et al. . |
| 5,688,831 | 11/1997 | El-Nokaly et al. . |
| 5,690,915 | 11/1997 | Eteve et al. . |

FOREIGN PATENT DOCUMENTS

| | | |
|---|---|---|
| 0 504 066 | 9/1992 | European Pat. Off. . |
| 0504066B1 | 9/1992 | European Pat. Off. . |
| 504066 | 9/1992 | European Pat. Off. . |
| 00369741 | 8/1994 | European Pat. Off. . |
| 0 856 305 A2 | 8/1998 | European Pat. Off. . |
| 2 686 510 | 7/1993 | France . |
| 2 280 605 | 2/1995 | United Kingdom . |
| WO93/18852 | 9/1993 | WIPO . |
| WO 93/23482 | 11/1993 | WIPO . |
| WO 95/04517 | 2/1995 | WIPO . |
| WO 96/33689 | 10/1996 | WIPO . |
| WO 99/22698 | 5/1999 | WIPO . |
| WO 99/24001 | 5/1999 | WIPO . |

*Primary Examiner*—Thurman K. Page
*Assistant Examiner*—S. Howard
*Attorney, Agent, or Firm*—Amway Corporation

[57] ABSTRACT

Makeup compositions having enhanced transfer resistance including at least one hydrophilic film former. The makeup can be a water-in-oil emulsion having the hydrophilic film former in the internal water phase and at least one pigment in the external oil phase. The makeup composition can also be a suspension of one or more cationically-coated pigments in water in which the hydrophilic film former is dissolved. The hydrophilic film former may also be an anionic gelling agent, whereby the cationically-coated pigment and the anionic gelling agent form a water-dispersable complex that upon application to the skin forms an insoluble pigmented salt having enhanced transfer resistance.

19 Claims, No Drawings

MAKEUP COMPOSITIONS AND METHODS OF MAKING SAME

BACKGROUND OF THE INVENTION

The present invention relates to makeup compositions and methods of making these compositions, and more particularly, to makeup compositions that incorporate one or more hydrophilic film formers.

Makeup compositions are applied as cosmetics to the skin to impart color, hide imperfections, even skin tone and texture, and accentuate or minimize features. Makeups include foundations, face powders, blushes, rouges, and eye shadows. Makeup compositions typically include pigments for coloring and may include other beneficial components, such as sunscreens, moisturizers, vitamins, and antioxidants.

Makeup compositions are available in several forms (e.g., powders, suspensions, dispersions, creams, and gels), but are often formulated as emulsions to provide the desired skin-feel, appearance, coverage, and moisturization attributes. Emulsion makeups typically contain pigments in the outer phase of the emulsion, so the consumer can clearly see the color of the makeup before application. If the pigments are in the inner phase of a makeup emulsion, then the outer phase may cloud, mask, or shift the true color of the makeup before application.

Emulsion cosmetics for skin application are typically water-in-oil emulsions because users prefer the soothing, powdery skin feel of an external oil phase over that of an external water phase. Accordingly, cosmetic pigments used in emulsions are coated or otherwise modified to be oil soluble so the pigment will reside in the external oil phase.

Applied makeups can flake or rub off over time to present a visually diminished appearance. The cosmetic user must then go to the trouble and expense of reapplying the makeup. Thus, cosmetic wearers desire makeups having good "transfer resistance"—that is, the ability to resist rubbing or flaking off to remain on the skin for longer periods.

To enhance transfer resistance, makeup compositions may include one or more "film formers," which are components that upon drying form a film to help bind or hold pigments or other components in place on the skin. Since makeup pigments are typically in the external oil phase of a cosmetic emulsion (as discussed above), the prevailing practice is to use hydrophobic (oil-soluble) film formers in makeups for skin applications. This is because it is widely believed that to enhance transfer resistance the film former should be dispersed in the same phase as the pigments residing in the external oil phase. Further, lipstick and sunscreen compositions use hydrophobic film formers since the environment of use (e.g., saliva and swimming pools) contain water that would dissolve a hydrophilic film former. See, for example, U.S. Pat. No. 5,250, 289 to Boothroyd entitled "Sunscreen Compositions" issued Oct. 5, 1993, which discloses a water-in-oil emulsion containing in the oil phase a oil-soluble film former (PVP/Hexadecene Copolymer—an alkylated polyvinyl pyrrolidone) and an oil-dispersable microfine titanium dioxide particles coated with aluminum stearate as sunscreen. (Examples 3–4.)

U.S. Pat. No. 4,665,107 to Micale entitled "Pigment Encapsulated Latex Aqueous Colorant Dispersions" discloses an oil-in-water emulsion eyeliner having a hydrophobic, oil-soluble film former (alkylated vinylpyrrolidone polymer) with a hydrophobic pigment (coated iron oxide) in the internal oil phase. However, since human skin produces oil over time—and more specifically since the sebaceous glands of the skin produce sebum—the fats and oils residing on the skin tend to resolubilize an oil-soluble film former and thus weaken the binding effect of the resulting film. Also, the use of oil-dispersable pigments may result in an undesirable color shift as the naturally produced skin oils resolubilize the pigments.

European Publication 504,066 published Sep. 16, 1992 entitled "Cosmetic Compositions Containing a Dispersion of Solid Particles Whose Surface is Covered by Means of a Cationic Polymer" discloses an oil-in-water emulsion mascara composition having a hydrophilic film former (hydroxyethylcellulose) in the external water phase with oil-dispersable cationic polymer-coated pigments dispersed in the internal oil phase. (Example J.) However, this mascara formulation suffers from the problem discussed above of a diminished color appearance before application because the pigment is in the internal phase rather than the external phase. Further, since the external phase first contacts the skin during makeup application, the film former in the external phase forms a film on the skin before the pigments are applied from the internal phase—thus resulting in a diminished transfer resistance because the film is under the pigments.

SUMMARY OF THE INVENTION

The aforementioned problems are overcome in the present invention wherein a water-in-oil makeup formulation includes at least one hydrophilic film former in the internal water phase and at least one pigment in the external oil phase. In one embodiment, the hydrophilic film former includes a salt of phenylbenzimidazole sulfonic acid ("PSA") to provide sunscreen attributes.

In another aspect of the present invention, a makeup composition includes at least one hydrophilic film former and at least one cationically-coated pigment dispersed in water. In one embodiment, the hydrophilic film former is an anionic gelling agent. The cationically-coated pigment is dispersed within the anionic gel to form a water-dispersable complex. As the user rubs or applies the formulation to the skin, two factors act to destabilize the complex and form a water-insoluble pigmented salt on the skin: 1) the evaporation of the water from the formulation and 2) the energy caused by rubbing or applying the formulation on the skin.

The incorporation of a hydrophilic film former in the internal water phase of a water-in-oil emulsion having pigments dispersed in the external oil phase provides enhanced transfer resistance. It is believed that the pigments in the outer phase—which first contact the skin upon application—are subsequently "sandwiched" by the film former in the internal water phase to improve the resistance to transfer. Since the hydrophilic film former is lipophobic, it will resist solubilization by the natural skin oils. Thus, the hydrophilic film former will last longer to provide effective transfer resistance. Further, the use of PSA as the hydrophilic film former also imparts sunscreen attributes to the composition.

The cationically-coated pigments of the aqueous dispersion bind to the naturally anionic charge of the skin to increase transfer resistance. Further, the hydrophilic, cationically-coated pigments resist absorbing the natural oil from the skin, which can cause an undesirable color-shift over time and also cause the pigments to "pool" or float in the skin oil. Surprisingly, the water-dispersion of cationically-coated pigments in an anionic gelling agent does not immediately form a water-insoluble salt, but rather forms a water-dispersable complex or gel-dispersion that upon application to the skin destabilizes to form a water-insoluble salt film providing superior transfer resistance.

These and other objects, advantages, and features of the invention will be more readily understood and appreciated by reference to the detailed description of the preferred embodiments.

DETAILED DISCUSSION OF THE PREFERRED EMBODIMENTS

The makeup composition according to a first aspect of the invention is a water-in-oil emulsion having an internal water phase containing a hydrophilic film former and an external oil phase containing a pigment. The makeup composition according to a second aspect of the invention is an aqueous suspension of the hydrophilic film former with cationically-coated pigments.

I. Water-in-Oil Emulsion

Water-in-oil emulsions contain an external "continuous" oil phase and an internal "discontinuous" water phase. The relative amounts of oil and water phase may vary widely so long as the resulting emulsion is a stable water-in-oil emulsion. Suitable amounts of oil phase include from about 10 to about 95 weight %, preferably from about 25 to about 75 weight %, and more preferably from about 44 to about 48 weight % oil phase based on the total weight of the emulsion, with corresponding amounts of water phase present. Water-in-oil emulsions and the methods of making them are well known to those of skill in the art. See, for example, U.S. Pat. No. 5,143,722 to Hollenberg issued Sep. 1, 1992 entitled "Cosmetic Makeup Compositions Comprising Water-In-Oil Emulsions Containing Pigment," U.S. Pat. No. 5,216,033 to Pereira issued Jun. 1, 1993 entitled "Water-In-Oil Transparent Emulsion For the Skin," and U.S. Pat. No. 5,599,533 to Stepniewski issued Feb. 4, 1997 entitled " Stable Water-In-Oil Emulsion System," each of which is incorporated herein in its entirety by reference.

A. External Oil Phase

The oil phase contains at least one cosmetically acceptable volatile oil—such as a mineral spirit, a synthetic oil, or a silicone oil (e.g., the dimethyl polysiloxane or cyclomethicone types)—in an amount effective to act as a carrier yet essentially evaporate. As used herein, "volatile" means evaporating readily at ambient (room) pressures and temperatures. Preferably the oil includes one or more silicone oils because of their non-greasy feel. The types and suitability of silicone oils for use in cosmetic water-in-oil emulsions are well known to those of skill in the art. Effective amounts of oil include from about 5 to about 90 weight %, preferably from about 15 to about 50 weight %, and more preferably from about 25 to about 35 weight % oil based on the total weight of the emulsion.

The oil phase also includes one or more oil-dispersable pigments, such as the hydrophobically-coated pigments whose surfaces are coated by or chemically bonded to a polysiloxane, for example, as described in Hollenberg '722 (cited above) and U.S. Pat. No. 4,578,266 to Tietjen issued Mar. 25, 1986 entitled "Silicone-Based Cosmetic Products Containing Pigment," which is incorporated herein in its entirety by reference. Preferred oil-dispersable pigments include the iron and titanium oxide pigments having a dimethicone exterior coating or a magnesium myristate exterior coating, both of which are available from Cardre Corporation. The oil-dispersable pigments are present in an amount, diameter size, and blend effective to achieve a desired coloring effect, as is known in the art. The effective amount of oil-dispersable pigment includes from about 3 to about 30 weight %, preferably from about 5 to about 15 weight %, and more preferably about 10 weight % pigment based on the total weight of the emulsion. The pigments are of the size effective for cosmetic use, for example from about 0.1 to about 60 microns, preferably from about 40 to about 60 microns for the metal oxide pigments.

The water-in-oil emulsion may contain one or more emulsifiers of a type and in an amount effective to maintain a stable water-in-oil emulsion. As is known in the art, the emulsifier (or blend of emulsifiers) is selected for its hydrophilic/lipophilic balance (HLB) attributes. Suitable emulsifiers include dimethicone copolyol and other emulsifier components described in Hollenberg '722 as "surfactants" and in Pereira '033, both cited above. Effective amounts of emulsifier include from about 0.2 to about 10 weight %, preferably about 1 weight % emulsifier based on the total weight of the emulsion. The water-in-oil emulsion may also include an effective amount of one or more coemulsifiers, for example, sorbitan trioleate. Effective amounts of coemulsifiers include from about 0.05 to about 5 weight %, preferably from about 0.1 to about 0.3 weight % coemulsifier.

B. Internal Water Phase

The major component of the water phase is water, preferably deionized water. The water phase includes from about 5 to about 90 weight %, preferably from about 25 to about 75 weight %, and more preferably from about 40 to about 50 weight % water based on the total weight of the emulsion.

The water phase includes an effective amount of at least one hydrophilic film former. As used herein, "film former" means a component that drys completely at room conditions to form a continuous, uniform, and non-tacky film that helps bind or hold particles or other components in place on the skin. In this sense, "film former" does not include all of the components that the prior art may refer to as film formers—for example, the components that merely increase the spreadability of a product to cover the skin (such as a sunscreen composition) or merely thickens the product. The differences between spreadability-enhancing (i.e., coverage-enhancing) components, thickeners, and film-forming components (as the term is used herein) are well-known to those of skill in the art. Preferably, the hydrophilic film former is capable of forming a pliant film. As used herein, "capable of forming a pliant film" means capable of forming on a glass slide at room temperature a continuous film that can be peeled or stripped by hand from the slide without breaking.

Hydrophilic film formers include: (1) water-soluble polyurethanes, such as C10 polycarbamyl polyglyceryl ester available, for example, from Rohm & Haas Corporation under the trademark ACULYN 44, (2) polyvinyl alcohol, (3) polyvinylpyrrolidone (PVP), (4) PVP copolymers, for example, vinyl pyrrilidone/vinyl acetate copolymers, such as PVP/vinyl acetate, (5) water-soluble acrylic acid copolymers and their esters and salts, for example the partial ester copolymers of acrylic/methacrylic acid and a polyethylene glycol ether of a fatty alcohol, such as acrylates/steareth-20 methacrylates copolymer available, for example, from Rohm & Haas under the trademark ACULYN 22, (6) organic and inorganic salts of phenylbenzimidazole sulfonic acid (PSA), such as TEA-phenylbenzimidazole sulfonate and sodium phenylbenzimidazole sulfonate, (7) water-soluble cellulosics, such as hydroxymethylcellulose, hydroxyethylcellulose, and hydroxypropylcellulose, (8) water-soluble quaterniums, such as polyquaternium-7, polyquaternium-10, polyquaternium-37, (9) carboxyvinyl polymers, such as carbomers and their salts, for example sodium carbomer, and (10) water-soluble polysaccharides, such as polydextrose and glucan. The hydrophilic film formers capable of forming a pliant film include C10 polycarbamyl polyglyceryl ester, polyvinyl alcohol, PVP, PVP/ vinyl acetate, acrylates/steareth-20 methacrylates copolymer, and TEA- and sodium-PSA.

Although PSA salts are known UV light-absorbing sunscreens, PSA salts as used in the present invention also act as hydrophilic film formers. PSA is available from Haarmann & Reimer under the trademark NEO HELIOPAN (type hydro). PSA itself is a water-insoluble powder; however, when dispersed in water with triethanolamine at a pH above 7, it forms the water-soluble salt TEA-PSA.

The hydrophilic film former in the water phase is present in an amount effective to enhance the transfer resistance of the makeup. Effective amounts of hydrophilic film former include from about 0.1 to about 8 weight %, preferably from about 0.8 to about 6 weight %, more preferably from about 1.5 to about 4 weight %, and most preferably about 2.5 to about 3.0 weight % hydrophilic film former.

Although the exact mechanism for the enhancement of the transfer resistance of the water-in-oil emulsion makeup is not known, it is believed that the external oil phase—which contains the pigments—is the first phase of the makeup to contact the skin upon application to deposit the pigments on the skin. Subsequently, the film former in the interior water phase forms a film that "sandwiches" the pigments to the skin under the film, thereby enhancing the transfer resistance.

C. Other Components

Either phase of the emulsion may also contain effective amounts of other cosmetically acceptable components, such as preservatives (e.g., diazolidinyl urea or one or more of the parabens), sunscreens, fragrances, humectants, colorants, emolients, skin conditioners, skin softeners, oil-control agents, antioxidants, and thickeners, so long as such components do not destabilize, break, or invert the emulsion.

Cosmetically acceptable sunscreens include the micronized sunscreen particles known in the art. The use of micronized particles to provide sunscreen protection in the present invention is particularly advantageous (i.e., where the sunscreen particles are included in the same phase as the pigment particles) because the sunscreen particles receive the benefit of enhanced transfer resistance, thereby prolonging the time that the particles are on the skin to provide protection. Examples of micronized sunscreen particles include: (1) oil-dispersable micronized zinc oxide coated with dimethicone, such as the sunscreen particles available from SUNSMART under the trademark Z-COTE HP1 having an average particle size of about 0.1 micron and (2) the water-dispersable micronized titanium dioxide particles, such as the sunscreen particles available from Kobo Corporation under product number BG45TC having a particle size of about 0.15 microns.

Effective amounts of sunscreen particles depends on the desired amount and length of sun protection, as is known in the art, and includes from about 1 to about 40 weight %, and preferably from about 3 to about 30 weight %, sunscreen particles based on the total weight of the makeup.

Other examples of sunscreens and micronized sunscreen particles are disclosed in U.S. Pat. No. 5,032,390 to Iwaya issued Jul. 16, 1991 entitled "Anti-Suntan Cosmetic Composition" and U.S. Pat. No. 5,188,831 to Nicoll issued Feb. 23, 1993 entitled "Sunscreens Containing Both Water and Oil Dispersable Titanium Dioxide Particles," each of which is incorporated herein in its entirety by this reference.

D. Forming the Emulsion

To make the water-in-oil emulsion: (1) mix the oil and oil-soluble components, except for the oil-dispersable pigments (and the sunscreen particles, if any), to form a homogenous oil mixture, (2) mix the oil-dispersable pigments (and sunscreen particles, if any) in the homogenous oil mixture to form a homogenous pigmented oil mixture, (3) mix the water and water-soluble components to form a homogenous water mixture, and (4) slowly add the water mixture to the pigmented oil mixture to form the water-in-oil emulsion while mixing carefully to avoid incorporating air in the emulsion. The manufacturer can mix the various components using, for example, a high shear mill or a high-speed stirring or dispersing apparatus, as is known in the art.

II. Aqueous Suspension

A second aspect of the present invention is an aqueous suspension of at least one hydrophilic film former with one or more cationically-coated pigments. As used herein, "aqueous suspension" means a single phase aqueous dispersion, suspension, or solution of components, which excludes emulsions having an oil phase.

A. Suspension Components

The suspension includes an amount of water (preferably deionized water) effective as a carrier vehicle in which to dissolve or suspend the other components of the formulation. Effective amounts of water include from about 30 to about 98 weight %, preferably from about 50 to about 90 weight % water based on the total weight of the suspension.

The suspension includes an effective amount of one or more hydrophilic film formers to enhance the transfer resistance of the makeup. Hydrophilic film formers and the effective amounts are discussed above with respect to the water-in-oil aspect of the present invention; that discussion also applies with respect to the water suspension aspect and is incorporated here. As previously discussed, the hydrophilic film former forms a film that is lipophobic. Thus, the film does not become solubilized by the skin oil and can remain on the skin for an extended period of time to assist the adherence of the pigments to the skin. Preferably the hydrophilic film former is capable of forming a pliant film.

The aqueous suspension also includes an effective amount of one or more cationically-coated pigments that are dispersable in water. "Cationically-coated pigments or particles" as used herein means pigments or particles having the pigment surface modified by coating, depositing, swelling onto, or chemically reacting with a cationic material. The cationic material includes cationic polyquaterniums. Examples of such pigments include the titanium and iron oxides available from Kobo Corporation under the "BG" series of pigments, which have a polyquaternium-7 coated on the pigment surface and are dispersed in butylene glycol. Cationically-coated particles are described in EP 504,066 published Sep. 16, 1992 entitled "Cosmetic Compositions Containing a Dispersion of Solid Particles Whose Surface Is Covered by Means of a Cationic Polymer," which is incorporated herein in its entirety by this reference.

The water-dispersable cationic pigments are present in an amount, diameter size, and blend effective to achieve a desired coloring effect. Effective amounts of cationically-coated, water-dispersable pigments include from about 3 to about 30 weight % and preferably from about 6 to about 13 weight % pigment based on the total weight of the suspension. The pigments are of the size for cosmetic use, for example, from about 0.1 to about 60 microns, preferably from about 40 to about 60 microns for the metal oxide pigments.

Since human skin typically has a negative charge (and since opposite charges attract), the cationically-coated pigments tend to adhere to the anionic charge of the skin. This adherence enhances the transfer resistance so that the pigments will stay in place for longer periods.

The particle coating must also permit the pigment to be dispersable in water. Since the coated pigment is hydrophilic (i.e., lipophobic), it will not absorb or become solubilized by the oil generated by the skin once applied. As discussed above, this allows the makeup to retain the same color and avoid "color shift" over time. Further, the pigment is much less likely to "pool" in the excess skin oil.

The suspension may also contain effective amounts of other cosmetically acceptable water-dispersable or soluble components, as discussed in conjunction with the water-in-oil makeup formulation above. For example, the suspension may also include effect amounts of cosmetically-acceptable sunscreen particles that are dispersable in water, preferably cationically-coated sunscreen particles. Cosmetically effective water-dispersable sunscreen particles and their effective amounts are discussed above. The present formulation will enhance the transfer resistance of the sunscreen particles in the same manner that it enhances the transfer resistance of the pigment particles.

B. Anionic Gel Film Former

In one embodiment of the aqueous suspension, at least one of the hydrophilic film formers is an anionic gel. The anionic gel swells when dispersed in water. Surprisingly, the cationically-coated pigments added to the anionic gel do not form an insoluble salt but rather form a water-dispersable complex or gel-dispersion. It is believed that the cationically-coated pigment is "trapped" in the complex. As the user rubs or applies the formulation to the skin, two factors act to destabilize the complex and form a water-insoluble pigmented salt on the skin: 1) the evaporation of the water from the formulation and 2) the energy resulting from the user applying or rubbing the formulation on the skin. The resulting pigment/film former salt film adheres to the skin with enhanced transfer resistance. Preferably the resulting hydrophilic film formed is a pliant film.

A suitable anionic gel is of a type capable of forming a water-dispersable complex with the cationically-coated pigments. Suitable anionic gels include: 1) the water-soluble acrylic acid copolymers and their derivatives, esters, and salts, for example, the acrylates copolymer available from Rohm & Haas under the trademark ACULYN 33 and the partial ester copolymers of acrylic/methacrylic acid and a polyethylene glycol ether of a fatty alcohol, such as the acrylates/steareth-20 methacrylates copolymer available from Rohm & Haas under the trademark ACULYN 22 and 2) carboxyvinyl polymers, such as carbomers and their salts, for example sodium carbomer. The anionic gels capable of forming a pliant cationic-pigment film include the acrylates/steareth-20 methacrylates copolymer.

The amount of anionic gel film former is that which is effective to enhance the transfer resistance of the resulting makeup, and to that extent includes the effective amounts of film former as discussed above. Preferably, the amount of anionic gel film former is that which is capable of complexing the amount of cationically-coated pigment present in the formulation. Such complexing-effective amounts of anionic gel film former includes from about 5 to about 150 weight %, preferably from about 10 weight % to about 100 weight %, more preferably from about 20 weight % to about 60 weight %, and most preferably about 25 weight % based on the amount of cationically-coated particles in the makeup suspension.

C. Forming the Suspension

To make the aqueous suspension: (1) mix the water and water-soluble components, except for the water-dispersable pigments (and the sunscreen particles, if any), to form a homogenous water mixture and (2) mix the water-dispersable cationically-coated pigments (and sunscreen particles, if any) one component at a time until all the particles are dispersed, carefully avoiding incorporating air in the suspension or over milling the suspension. The manufacturer can mix the various components using, for example, a high shear mill or a high-speed stirring or dispersing apparatus, as is known in the art. If under step 1 the hydrophilic film former is an anionic gel, then the resulting gel preferably is adjusted to have a pH of from about 4 to about 7, preferably about 6, before the addition of cationically-coated particles.

The following examples are presented for the purpose of further illustrating and explaining the present invention and are not to be taken as limiting in any regard. Unless otherwise indicated, all parts and percentages are by weight.

EXAMPLE 1

A water-in-oil emulsion makeup foundation was prepared by individually preparing each of the following parts as set forth below. The weight percentages are based on the total formulation:

| Component | Weight % |
|---|---|
| Part A | |
| Cyclomethicone carrier | 20.00 |
| Dimethicone Copolyol emulsifier | 1.00 |
| with Cyclomethicone | 9.00 |
| Part B | |
| Titanium Dioxide (Dimethicone Coating) pigment (40 micron average diameter) | 8.33 |
| Iron Oxide Yellow (Dimethicone Coating) pigment (40–60 micron average diameter) | 1.35 |
| Iron Oxide Red (Dimethicone Coating) pigment (40–60 micron average diameter) | 0.26 |
| Iron Oxide Black (Dimethicone Coating) pigment (40–60 micron average diameter) | 0.06 |
| Zinc Oxide (Dimethicone Coating) sunscreen particle (0.1 micron average diameter) | 5.00 |
| Part C | |
| Deionized Water | 42.45 |
| Phenylbenzimidazole Sulfonic Acid Solution with: | |
| Deionized Water | 5.20 |
| Triethanolamine | 1.80 |
| Phenylbenzimidazole Sulfonic Acid film former/sunscreen | 3.00 |
| Polysorbate-20 surfactant | 0.05 |
| Part D | |
| Diazolidinyl Urea, methylparaben, propylparaben, and propylene glycol preservatives (optional) | 0.50 |
| Part E | |
| Silica (Kobo Corporation number MSS 500/3H) oil absorbent (2.4 micron) (optional) | 1.00 |
| Silica (Kobo Corporation number MSS 500/3N) oil absorbent (3.8 micron) (optional) | 1.00 |

Each of parts A–E was individually formed at room temperature by mixing until homogenous. Part B was added to Part A, then mixed until homogenous. Part C was added with the combined Parts AB, then slowly mixed until homogenous. Thereafter, optional Part D was added as preservative to the combined Parts ABC, then mixed until homogenous. Thereafter, optional Part E was added to provide oil-absorbency to the combined Parts ABCD, then mixed until homogenous. The resulting water-in-oil emulsion was stable with enhanced transfer resistance.

EXAMPLE 2

A water-in-oil emulsion makeup foundation was prepared by individually preparing each of the following parts as set forth below. The weight percentages are based on the total formulation:

| Component | Weight % |
|---|---|
| Part A | |
| Cyclomethicone | 20.00 |
| Dimethicone Copolyol emulsifier with Cyclomethicone | 1.00 9.00 |
| Sorbitan Trioleate coemulsifier | 0.20 |
| Acrylates Copolymer non-surfactant suspending agent (POLYTRAP 6603 by Dow Corning) (optional) | 2.00 |
| Part B | |
| Titanium Dioxide (Magnesium Myristate coating) pigment (40 micron average diameter) | 8.69 |
| Iron Oxide Black (Magnesium Myristate coating) pigment (40–60 micron average diameter) | 0.12 |
| Iron Oxide Yellow (Magnesium Myristate coating) pigment (40–60 micron average diameter) | 0.84 |
| Iron Oxide Red (Magnesium Myristate coating) pigment (40–60 micron average diameter) | 0.35 |
| Zinc Oxide (Dimethicone Coating) sunscreen particle (0.1 micron average diameter) | 3.00 |
| Part C | |
| Deionized Water | 36.30 |
| Glycerin humectant (optional) | 2.00 |
| Green Tea Extract antioxidant (optional) | 1.00 |
| Acerola Extract antioxidant (optional) | 1.00 |
| Alpha Glucan Oligosaccarhides (encourages growth of beneficial skin flora) (optional) | 2.00 |
| C10 Polycarbamyl Polyglyceryl Ester hydrophilic film former | 1.00 |
| Phenylbenzimidazole Sulfonic Acid Solution with: | |
| Deionized Water | 5.20 |
| Triethanolamine | 1.80 |
| Phenylbenzimidazole Sulfonic Acid film former/sunscreen | 3.00 |
| Benzyl Alcohol preservative (optional) | 1.50 |

Each of parts A–C was individually formed at room temperature with mixing until homogenous. Part B was added to Part A, then mixed until homogenous. Thereafter, Part C was added slowly to the combined Parts AB, then slowly mixed until forming the stable water-in-oil emulsion having enhanced transfer resistance.

EXAMPLE 3

An aqueous suspension makeup foundation was prepared by individually preparing each of the following parts as set forth below. The weight percentages are based on the total formulation:

| Component | Weight % |
|---|---|
| Part A | |
| Deionized Water | 84.50 |
| Acrylates/Steareth-20 Methacrylates Copolymer anionic gelling agent/film former | 3.00 |
| Part B | |
| Triethanolamine 99% | q.s. pH 6.00 |
| Part C | |
| Titanium Dioxide pigment (0.20–0.25 microns) cationically-coated* | 9.00 |
| Iron Oxide Black (0.37–0.43 microns) cationically-coated* | 0.10 |
| Iron Oxide Yellow (0.29–0.35 microns) cationically-coated* | 3.00 |
| Iron Oxide Red (0.20–0.25 microns) cationically-coated* | 0.40 |

*Available from Kobo Corporation under the "BG" series of pigments, having a polyquaternium-7 coating on the pigment surface and dispersed in butylene glycol.

Each of parts A and C was individually formed at room temperature with mixing until homogenous. Thereafter, Part B was added to Part A, then mixed until clear without incorporating air. Thereafter, Part C was added one component at a time while mixing. The combined Parts ABC are milled until the pigments are dispersed without over milling. The resulting stable suspension contained a complex of the gelling agent with the cationically-coated pigments. Upon application of the suspension to skin and evaporation of the water, the complex formed a water-insoluble gelling agent/film former salt on the skin having enhanced transfer resistance.

EXAMPLE 4

An aqueous suspension makeup foundation was prepared by individually preparing each of the following parts as set forth below. The weight percentages are based on the total formulation:

| Component | Weight % |
|---|---|
| Part A | |
| Deionized Water | 58.45 |
| Green Tea Extract antioxidant (optional) | 1.00 |
| Acerola Extract antioxidant (optional) | 1.00 |
| Alpha Glucan Oligosaccarhides (encourages growth of beneficial skin flora) (optional) | 2.00 |
| C10 Polycarbamyl Polyglyceryl Ester hydrophilic film former | 0.50 |
| Styrene/DVB Copolymer oil absorbent (optional) | 2.00 |
| Part B | |
| Titanium Dioxide sunscreen particles (0.13–0.16 microns) cationically-coated* | 27.00 |
| Titanium Dioxide pigment (0.20–0.25 microns) cationically-coated* | 4.00 |
| Iron Oxide Black (0.37–0.43 microns) cationically-coated* | 0.15 |
| Iron Oxide Yellow (0.29–0.35 microns) cationically-coated* | 2.00 |
| Iron Oxide Red (0.20–0.25 microns) cationically-coated* | 0.40 |
| Part C | |
| Benzyl Alcohol preservative (optional) | 1.50 |

*Available from Kobo Corporation under the "BG" series of pigments/particles, having a polyquaternium-7 coated on the pigment surface and dispersed in butylene glycol.

Each of parts A and B was individually formed at room temperature by mixing until homogenous. Thereafter, optional Part C was added to Part A as a preservative, then mixed until homogenous. Thereafter, Part B was added to the combined Parts AC, then mixed until the pigments are dispersed without over milling. The resulting stable suspension exhibited enhanced transfer resistance.

The above descriptions are those of preferred embodiments of the invention. Various alterations and changes can be made without departing from the spirit and broader aspects of the invention as defined in the claims, which are to be interpreted in accordance with the principles of patent law, including the doctrine of equivalents.

The embodiments of the invention in which an exclusive property or privilege is claimed are defined as follows:

1. A water-in-oil makeup emulsion comprising:

an external oil phase having a volatile oil and at least one particle dispersed in the oil; and an internal water phase having water and an effective amount of at least one hydrophilic film former dispersed in the water, wherein the hydrophilic film former is selected from the group consisting of water-soluble polyurethanes, polyvinyl alcohol, polyvinylpyrrolidone, PVP copolymers, water-soluble acrylic acid copolymers and their esters and salts, organic and inorganic salts of phenylbenzimidazole sulfonic acid, water-soluble quaterniums, carboxyvinyl polymers, and mixtures thereof.

2. The makeup emulsion of claim 1 wherein the particle is a pigment and the emulsion includes a cosmetically effective amount of pigment.

3. The makeup emulsion of claim 1 wherein the particle is a sunscreen particle and the emulsion includes an sunscreen effective amount of sunscreen particle.

4. The makeup emulsion of claim 1 wherein the hydrophilic film former is selected from the group consisting of the organic and inorganic salts of phenylbenzimidazole sulfonic acid, and mixtures thereof.

5. The makeup emulsion of claim 1 wherein the particle contains a silicone coating.

6. The makeup emulsion of claim 1 wherein the external oil phase lacks a film former.

7. The makeup emulsion of claim 1 wherein:

the oil phase includes from about 25 to about 35 weight % cyclomethicone, from about 0.2 to about 10 weight % emulsifier, from about 5 to about 10 weight % oil-dispersable pigment, and a sunscreen effective amount of oil-dispersable sunscreen particle; and the water phase includes from about 40 to about 50 weight % water, from about 0.5 to about 1.5 weight % C10 polycarbamyl polyglyceryl ester, and from about 2.5 to about 3.5 weight % of a salt of phenylbenzimidazole sulfonic acid, wherein all percentages based on the total weight of the emulsion.

8. The makeup emulsion of claim 1 wherein the hydrophilic film former consists essentially of a compound from the group consisting of the organic and inorganic salts of phenylbenzimidazole sulfonic acid, and mixtures thereof.

9. The makeup emulsion of claim 1 wherein:

the oil phase includes about 25 to about 35 weight % cyclomethicone, from about 0.2 to about 10 weight % emulsifier, from about 5 to about 10 weight % oil-dispersable pigment, and a sunscreen effective amount of oil-dispersable sunscreen particle; and to the water phase includes from about 40 to about 50 weight % water and from about 2.5 to about 3.5 weight % of a salt of phenylbenzimidazole sulfonic acid, wherein all percentages based on the total weight of the emulsion.

10. The composition of claim 1 wherein the oil phase includes an oil carrier consisting essentially of one or more volatile oils.

11. The composition of claim 1 wherein the hydrophilic film former is capable of forming a pliant film.

12. A makeup composition comprising:

water;

an effective amount of at least one hydrophilic film former dispersed in the water, wherein the hydrophilic film former is selected from the group consisting of water-soluble polyurethanes, polyvinyl alcohol, polyvinylpyrrolidone, PVP copolymers, water-soluble acrylic acid copolymers and their esters and salts, organic and inorganic salts of phenylbenzimidazole sulfonic acid, water-soluble quaterniums, carboxyvinyl polymers, and mixtures thereof; and one or more cationically-coated particles dispersed in the water with the hydrophilic film former.

13. The makeup composition of claim 12 further comprising:

from about 50 to about 90 weight % water;

from about 0.2 to about 0.8 weight % of C10 polycarbamyl polyglyceryl ester as hydrophilic film former;

from about 2 to about 18 weight % of water-dispersable cationically-coated pigment; and a sunscreen effective amount of water-dispersable sunscreen particles.

14. The makeup composition of claim 12 wherein at least one hydrophilic film former is an anionic gelling agent capable of forming a water-dispersable complex with the cationically-coated particles.

15. The makeup composition of claim 14 wherein:

the makeup composition is an aqueous suspension; and the hydrophilic film former is capable of forming a pliant film of a water-insoluble salt with the cationically-coated particles upon evaporation of the water.

16. A method of forming a makeup composition comprising:

forming an aqueous suspension by mixing a complexing-effective amount of at least one hydrophilic film former that is an anionic gelling agent with water to form a water-dispersable gel; and dispersing a plurality of cationically-coated particles in the gel.

17. The makeup composition formed by the method of claim 16.

18. A method of applying a makeup composition comprising applying the makeup composition of claim 17 to skin, wherein the water evaporates to form a water-insoluble salt of the cationically-coated pigment and hydrophilic film former on the skin.

19. The makeup emulsion of claim 1 wherein the hydrophilic film former comprises phenylbenzimidazole sulfonic acid and water soluble polyurethanes and mixtures thereof.

* * * * *

UNITED STATES PATENT AND TRADEMARK OFFICE
CERTIFICATE OF CORRECTION

PATENT NO. : 6,132,739
DATED : October 17, 2000
INVENTOR(S) : Jesse C. Leverett

It is certified that error appears in the above-identified patent and that said Letters Patent is hereby corrected as shown below:

Column 11,
Claim 9, before "the water phase" delete -- [to] --

Signed and Sealed this

Ninth Day of October, 2001

Attest:

*Nicholas P. Godici*

NICHOLAS P. GODICI
*Attesting Officer*   Acting Director of the United States Patent and Trademark Office